United States Patent [19]
Lee

[11] Patent Number: 5,290,510
[45] Date of Patent: Mar. 1, 1994

[54] DEDORIZING DEVICE AND METHOD FOR THE THAWING COMPARTMENT OF A REFRIGERATOR

[75] Inventor: Cha J. Lee, Kyungki, Rep. of Korea

[73] Assignee: Samsung Electronics Co., Ltd., Suwon, Rep. of Korea

[21] Appl. No.: 6,537

[22] Filed: Jan. 21, 1993

[30] Foreign Application Priority Data

Feb. 1, 1992 [KR] Rep. of Korea ............... 92-1644

[51] Int. Cl.$^5$ ............................................. A61L 9/00
[52] U.S. Cl. ................................. 422/5; 422/4; 422/122; 99/474
[58] Field of Search ............... 422/4, 5, 120, 122, 422/220; 99/474

[56] References Cited

U.S. PATENT DOCUMENTS

| | | | |
|---|---|---|---|
| 3,691,346 | 9/1972 | Dyre et al. | 422/122 X |
| 4,023,928 | 5/1977 | Haensel | 422/122 X |
| 4,584,177 | 4/1986 | Fernbach et al. | 422/220 X |
| 4,727,801 | 3/1988 | Yokoi et al. | 99/474 X |
| 4,948,567 | 8/1990 | Atarashiya | 422/120 X |

FOREIGN PATENT DOCUMENTS

| | | | |
|---|---|---|---|
| 402052022 | 2/1990 | Japan | 422/122 |
| 2-194816 | 8/1990 | Japan | 422/120 |

*Primary Examiner*—Robert J. Warden
*Assistant Examiner*—E. Leigh Dawson
*Attorney, Agent, or Firm*—Burns, Doane, Swecker & Mathis

[57] ABSTRACT

A refrigerator includes a thawing compartment in which food is to be thawed through the aid of a heater. An odor absorbing member mounted along a ceiling of the compartment comprises a porous plate which carries a platinum catalyst. The catalyst absorbs odors which are decomposed upon being heated to more than 100° C. by the heater. Upon being heated greater than 250° C. the odors form a platinum-sulfur compound which attaches to the porous plate.

10 Claims, 2 Drawing Sheets

DEDORIZING DEVICE AND METHOD FOR THE THAWING COMPARTMENT OF A REFRIGERATOR

TECHNICAL FIELD

The present invention relates to a deodorizing device and method for the thawing compartment of a refrigerator.

BACKGROUND ART

A thawing compartment of some refrigerators that thaws frozen foodstuffs is located in the upper section of the cooling compartment, said thawing compartment being enclosed in a case which provides an interior space for storing foodstuffs and maintaining an atmosphere conducive to thawing foodstuffs.

Said thawing compartment has a cover at the front side to provide easy access for inserting or withdrawing foodstuffs and has an inlet in the rear surface to admit a portion of the cool air as it passes to the cooling compartment.

An outlet is provided at the front of the ceiling of the thawing compartment to provide an air passage which directs the cool air to an evaporator after the cool air has passed in through the inlet and has contacted with the foodstuffs in the compartment.

Also, a heater is installed in the middle portion of the ceiling of the thawing compartment to facilitate quick-thawing.

Thus, the thawing compartment constructed as described above thaws foodstuffs either slowly or quickly.

For example, foodstuffs are thawed slowly when a portion of the cool air which flows to the cooling compartment is diverted into the thawing compartment, whereas foodstuffs are thawed quickly by the operation of the heater.

But, according to the prior art unpleasant odors are often emitted by foodstuffs such as fish, shellfish, or meat and the odors circulate throughout the interior of the refrigerator when foodstuffs are stored in the thawing compartment.

The unpleasant odors in the cooling and the freezing compartments as well as the thawing compartment impair the freshness of other foodstuffs stored in the refrigerator, and this gives the user an unfavorable feeling, and also creates an unsanitary condition.

SUMMARY OF THE PRESENT INVENTION

The first object of the present invention is to provide a deodorizing device in the thawing compartment of a refrigerator, thereby eliminating the odors emitted by foodstuffs stored in the thawing compartment.

The second object of the present invention is to provide a method for eliminating the odors emitted by the foodstuffs in the thawing compartment of a refrigerator by the interaction of a deodorizing member and a heater, both of which are components of a deodorizing device.

The third object of the present invention is to provide a deodorizing device and method which are able to completely absorb odors emitted by foodstuffs in the thawing compartment during the entire lifetime of the refrigerator.

The deodorizing device for the thawing compartment of a refrigerator according to the present invention comprises: a deodorizing member which is installed over the entire surface of the ceiling of the thawing compartment for eliminating odors emitted by the foodstuffs, a heater which is installed along the transverse center-line of the deodorizing member for thawing the foodstuffs, a heat-reflecting plate which is attached to the back side of the deodorizing member for reflecting heat generated by the heater through a number of openings formed in the deodorizing member, and a stiff protecting net formed in a tetragonal shape which is attached to the front side of the deodorizing member for protecting the heater and the deodorizing member from damage.

The deodorizing member is manufactured by spraying a platinum catalyst on the surface of a catalyst support which is made by press-forming a porous substance and then sintering it.

The concave portion of the transversely semi-cylindrical shape is formed at the center part of the deodorizing member, with both sides forming a tetragonal plane.

A number of tetragonal openings are made at regular intervals at the concave portion of the deodorizing member in order to expose the heat-reflecting plate to the foodstuffs, and a number of holes are arranged at equal intervals on the one side of the deodorizing member, which will be positioned at the front of the ceiling of the thawing compartment, in order to provide air passages for the cool air, which has flowed into the thawing compartment, to leave the compartment through an outlet.

By the deodorizing device constructed as described above, any unpleasant odors emitted by foodstuffs in the refrigerator (such as mercaptan (molecular formula $CH_3SH$) etc.) are eliminated by the several steps as follows: a) circulating a portion of the cool air, which is directed toward the cooling compartment, into the thawing compartment through an inlet, b) mixing the cool air with any odors emitted by foodstuffs and then circulating the mixed air through the thawing compartment, c) physically absorbing the odors in the mixed air by a platinum catalyst and a catalyst support, and discharging refreshed air to an intermediate compartment through an outlet, d) thermally and chemically decomposing the absorbed odors into sulfur dioxide gas, sulfurous acid gas etc. by heating the air to more than 100 deg. C. by the operation of the heater, e) composing a platinum-sulfur chemical compound from the gases and attaching it to the catalyst support as the thermally decomposed gases are heated to more than 250 deg. C.

Further, the deodorizing member can be used indefinitely without being replaced with another one during the entire lifetime of the refrigerator because it is able to semi-permanently absorb the odors emitted by the foodstuffs in the thawing compartment.

As described above, the deodorizing device according to the present invention keeps foodstuffs fresh and permits the user to use the refrigerator in a pleasant atmosphere by eliminating odors emitted by foodstuffs in the thawing compartment.

Also, the deodorizing device never requires maintenance because the deodorizing device and method are plain and simple, and it is not necessary to replace any of its parts during the entire lifetime of the refrigerator.

DETAILED DESCRIPTION OF THE PREFERRED EMBODIMENT

Figure 1:
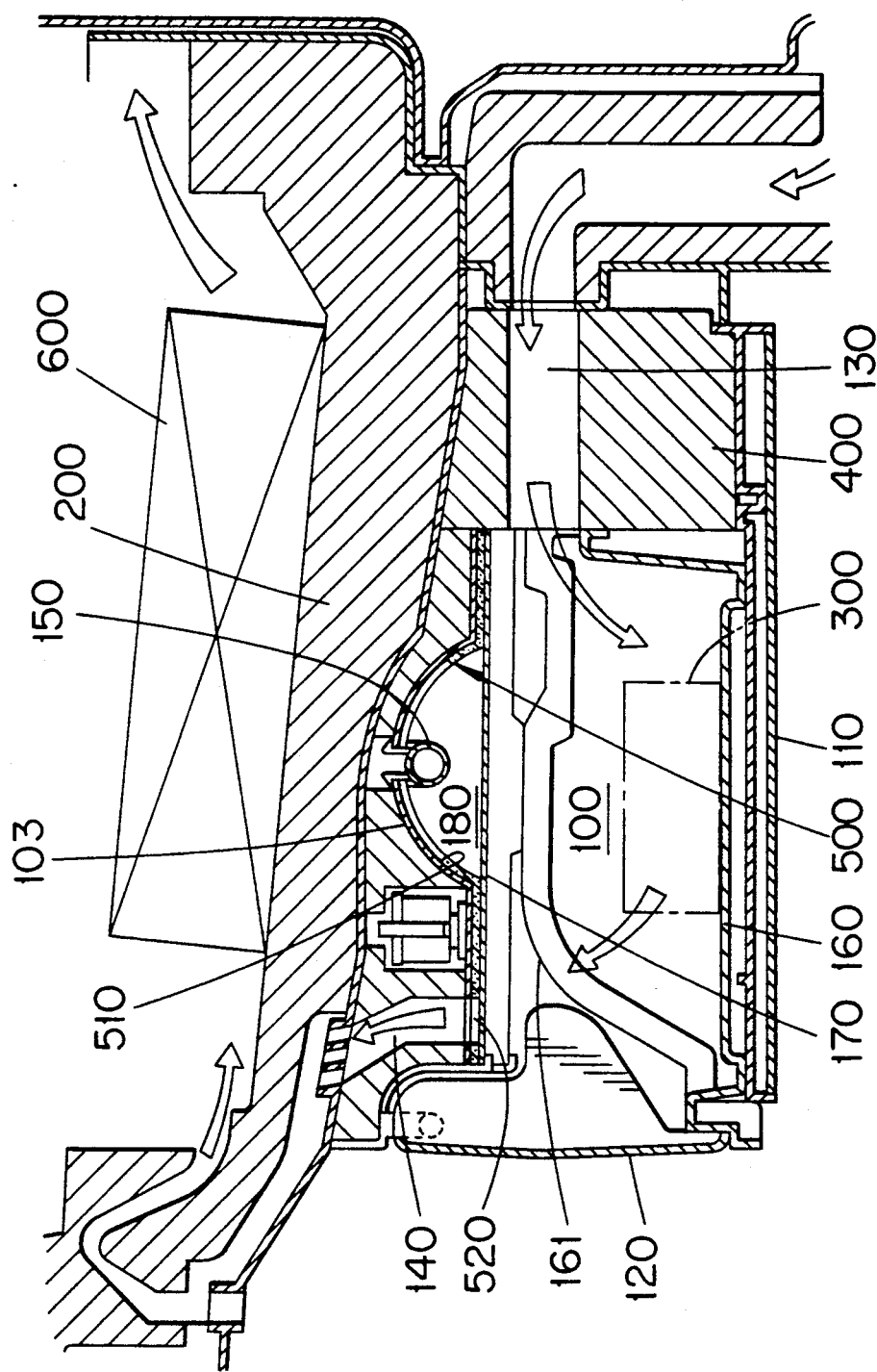
FIG. 1 is an enlarged cross sectional view of the thawing compartment of a refrigerator showing the construction of the thawing compartment and the stream of cool air according to the present invention.

FIG. 1 is an enlarged cross sectional view showing a thawing compartment 100 of a refrigerator in which a deodorizing device 180 is installed.

The thawing compartment 100 is installed in the upper area of the cooling compartment and a separate thawing atmosphere is maintained by a case shield 110.

A cover 120, capable of being moved up and down, is provided at the front of the thawing compartment 100 for inserting and withdrawing foodstuffs 300, and an inlet 130 is provided at the back of the compartment for allowing a portion of the cool air flowing to the cooling compartment to enter the thawing compartment 100.

An outlet 140 is provided in the front area of the ceiling of the thawing compartment 100 for circulating the cool air, which entered through the inlet 130, into an evaporator 600 positioned in an intermediate compartment 200.

A heat-reflecting plate 103 which is installed over the entire surface of the ceiling in accordance with the shape of the ceiling improves the thawing efficiency by reflecting the heat generated by a heater 150 toward the foodstuffs 300.

Further, the thawing compartment 100 maintains a separate thawing atmosphere without affecting the cooling compartment and the intermediate compartment 200 because the upper and the lower parts of the thawing compartment 100 are shielded by an insulating member 400.

A tray 160, on which a foodstuff 300 which is to be thawed will be placed, is mounted on the bottom of the thawing compartment 100 to act as a drawer, and partitions 161 mounted on both sides of the tray 160 are installed to form sliding contact with an open/closing type cover 120 which can be moved up and down, and therefore the cover 120 becomes opened or closed according to the back/forth movement of the tray 160.

In order to protect the heater 150 transversely mounted on the center portion of the ceiling and a deodorizing member 500 which will be described in detail later, a tetragonal shaped protecting net 170 is attached to the front of the deodorizing member 500.

The deodorizing member 500 is installed so as to extend over the entire surface of the ceiling of the thawing compartment 100 constructed as described above, with the heat-reflecting plate 103 being attached to the back or upper side of the deodorizing member 500.

Figure 2:
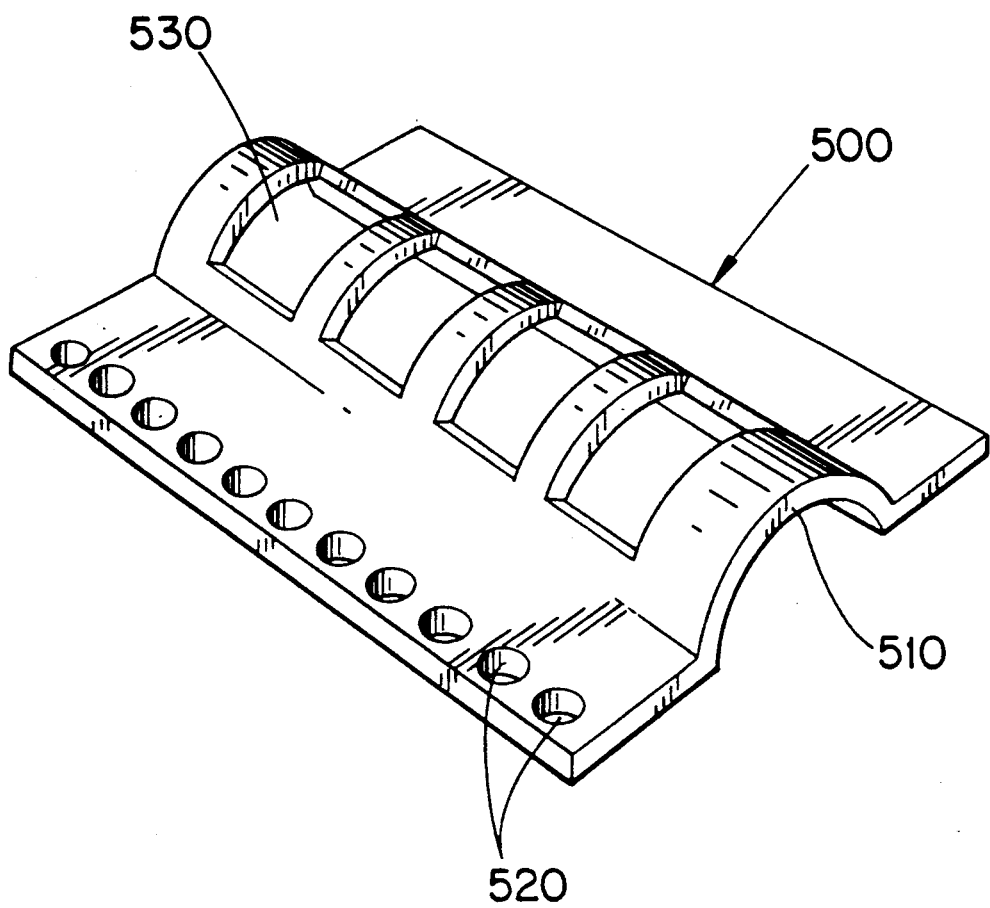
FIG. 2 is a perspective view illustrating a deodorizing member according to the present invention.

This deodorizing member 500 which is formed with a flat plate in a tetragonal shape as illustrated in FIG. 2, has a concave portion 510 of a semi-cylindrical shape at its center in accordance with the concave shape formed on the ceiling of the thawing compartment 100. A number of openings 530 are formed at regular intervals on the wall surface of the concave portion 510 in order to communicate the heat-reflecting plate 103 with the floor. The openings 530 form a straight path through the member 500 so that the reflected heat traveling along the path will not encounter the member 500.

There are also arranged at equal intervals at the one side of the deodorizing member 500 a number of holes 520 for providing air passage ways which connect the inside of the thawing compartment 500 with the intermediate compartment 200 in order to facilitate the circulation of cool air.

The deodorizing member 500 is manufactured by spraying a catalyst such as platinum etc. on the surface of a catalyst support which is made by press-forming a porous substance such as diatom earth etc. and then sintering it.

The deodorizing device 180 constructed as described above eliminates the odors emitted by foodstuffs in the thawing compartment 100 such as fish, shellfish, or meat, through the process of deodorizing as described below.

That is, a portion of the cool air coming into the cooling compartment flows into the thawing compartment 100 through the inlet 130 and circulates inside the thawing compartment 100.

And at this time, mercaptan(CH3SH), a typical odor emitted by foodstuffs 300 as fish, shellfish, or meat is mixed and circulated with the flowing cool air, and then the odor is physically absorbed by the deodorizing member 500 which is attached to the ceiling of the thawing compartment 100.

Accordingly, only refreshed air is discharged to the evaporator 600 installed on the intermediate compartment 200 through the outlet 140 on the front side of the ceiling of the thawing compartment 100.

The unpleasant odors such as Mercaptan(CH3SH) etc. physically absorbed by the platinum catalyst and the catalyst support, which are components of the deodorizing member 500, are decomposed into several gases such as sulfur dioxide and sulfurous acid etc. by being heated to more than 100 deg. C. by the heater 150 which also operates to thaw foodstuffs 300.

When the decomposed gases are heated to more than 250 deg. C., they are again divided into a platinum-sulfur chemical compound, and colorless and odorless components such as carbon dioxide, oxygen etc.

Here, the platinum-sulfur chemical compound attaches to the catalyst support and only the colorless and odorless components are discharged to the outside, and consequently the odors emitted by foodstuffs 300 are completely eliminated.

Additionally, the deodorizing member 500 is capable of being used indefinitely without being replaced because the deodorizing member 500 can absorb the odor components continually emitted by foodstuffs 300, completely receiving the platinum-sulfur chemical compound accumulated during the entire lifetime of the refrigerator.

What is claimed is:

1. A food thawing compartment in a refrigerator, comprising means defining a compartment, an air inlet and an air outlet communicating with the compartment, said compartment including a ceiling overlying a food containing portion of said compartment, an odor absorbing member disposed on the ceiling, a food-thawing heater disposed beneath a portion of said odor absorbing member and above said food containing portion of said compartment, a heat reflecting plate disposed above said odor absorbing member for reflecting heat downwardly toward said food containing portion through openings in said odor absorbing member, said openings defining straight paths through said odor absorbing member, and a protective net disposed beneath said heater and extending across a lower face of said odor absorbing member.

2. A food thawing compartment according to claim 1, wherein said odor absorbing member comprises a plate having an odor absorbing catalyst thereon.

3. A food thawing compartment according to claim 2, wherein said catalyst comprises a platinum catalyst.

4. A food thawing compartment according to claim 3, wherein said plate comprises a porous substance.

5. A food thawing compartment according to claim 1, wherein said odor absorbing member defines a recess in which said heater is disposed.

6. A food thawing compartment according to claim 1, wherein said ceiling includes a recess in which said odor absorbing member and said heater are disposed.

7. A food thawing compartment according to claim 6, wherein said protective net extends across a lower portion of said recess.

8. A method of eliminating odors in a thawing compartment of a refrigerator, comprising the steps of:

circulating cool air through a compartment of a refrigerator such that the air becomes mixed with odors from food disposed in said compartment;

heating and decomposing odors within the compartment while simultaneously thawing food disposed in a food containing portion of the compartment;

absorbing the decomposed odors by a platinum catalyst and catalyst support disposed in said compartment; and reflecting heat downward toward said food containing portion along straight paths through openings disposed in said catalyst support and catalyst.

9. A method according to claim 8, wherein the odors are decomposed into sulfur dioxide gas and sulfurous acid gas by being heated to more than 100° C.

10. A method according to claim 8, wherein the odors are decomposed into a platinum-sulfur compound by being heated to more than 250° C. and are absorbed by a porous catalyst support which carries the catalyst.

* * * * *